United States Patent
Herbst

(10) Patent No.: US 11,504,262 B2
(45) Date of Patent: Nov. 22, 2022

(54) DEVICE FOR IMPROVING RESPIRATION

(71) Applicant: Martin Herbst, Lofer (AT)

(72) Inventor: Martin Herbst, Lofer (AT)

( * ) Notice: Subject to any disclaimer, the term of this patent is extended or adjusted under 35 U.S.C. 154(b) by 224 days.

(21) Appl. No.: 17/084,013

(22) Filed: Oct. 29, 2020

(65) Prior Publication Data

US 2021/0220161 A1    Jul. 22, 2021

(30) Foreign Application Priority Data

Jan. 17, 2020  (EP) ..................................... 20152365

(51) Int. Cl.
*A61F 5/08* (2006.01)

(52) U.S. Cl.
CPC ...................................... *A61F 5/08* (2013.01)

(58) Field of Classification Search
CPC ............... A61F 5/08; A61F 5/56; A61F 5/566
See application file for complete search history.

(56) References Cited

U.S. PATENT DOCUMENTS

| 2009/0093840 A1 | 4/2009 | Macdonald |
| 2010/0331777 A1* | 12/2010 | Danielsson ............ A62B 23/06 |
| | | 606/199 |
| 2014/0326244 A1* | 11/2014 | Orts Paya ................. A61F 5/08 |
| | | 606/199 |

FOREIGN PATENT DOCUMENTS

| DE | 202008010203 U1 | 11/2008 |
| KR | 200474564 Y1 | 9/2014 |
| WO | 2014009985 A1 | 1/2014 |

OTHER PUBLICATIONS

European Patent Office, Search Report, 6 pages, EP 20152365 dated May 12, 2020.

* cited by examiner

*Primary Examiner* — Majid Jamialahmadi
(74) *Attorney, Agent, or Firm* — Middleton Reutlinger

(57) ABSTRACT

Embodiments described herein to a device for improving respiration comprising at least one nasal insert provided to be inserted into a nostril of a user, wherein the at least one nasal insert comprises a conical base body, a through-hole extending along the main axis of the base body, and a spiral element arranged on the inside of the base body and extending from the base of the base body to the tip of the base body.

12 Claims, 4 Drawing Sheets

DEVICE FOR IMPROVING RESPIRATION

TECHNICAL FIELD

The present disclosure relates to a device for improving the respiration of a user. The present disclosure further relates to the use of such a device for improving the respiration.

BACKGROUND

The nose belongs anatomically to the outer and upper respiratory tracts and is an important part of the human respiratory system. It includes the nostrils and the nasal cavity, wherein the nostrils lead into the interior of the nose, first into the nasal vestibule and then into the actual nasal cavity. The nasal cavity is divided into two separate sections by the nasal septum and is lined by a mucous membrane. The left and right nasal cavity are each subdivided by the bony supported nasal conchae, which define three nasal passages. The upper nasal passage, also called olfactory passage, includes the olfactory organ in its rear part, and the middle nasal passage leads into the paranasal sinuses. The lower nasal passage is the largest of the three nasal passages.

Although all nasal passages lead via the choanae openings into the nasopharynx and thus serve as airways, most of the respiratory air is transported via the lower nasal passage, as it is the most direct passage from the nasal opening to the nasopharynx due to its size and location. Therefore, the lower nasal passage is also called the respiratory passage.

A narrowing or other anatomical change in the nasal cavity or the nasal passages often leads to an impairment of breathing through the nose. There can be many reasons for such a narrowing. For example, it can occur due to a swelling of the mucous membranes of the nasal cavity during rhinitis or a cold. For example, a curvature of the nasal septum can also lead to asymmetrical flow conditions in both halves of the nose. Such changes can, for example, impair recovery during sleep, since not enough air can be taken in through the nose. They can also manifest in snoring during sleep.

Devices to improve respiration through the nose are generally known. EP 3 498 237 A1, for example, discloses a tubular device that is inserted into a nasal passage and can thus give it a desired shape. Thereby, an improved air flow through the nose is supposed to be achieved. This known device is individually adapted for patients in order to optimally shape the nasal passage.

However, this tubular device is almost completely inserted into the nasal passage. Therefore, its use, especially its removal, is complicated. Furthermore, although the known device can compensate for any narrowing of the nasal passage, it does not allow for improved respiration if the nasal passage is not narrowed or blocked. Furthermore, as mentioned above, this device has to be adapted individually for each patient, which makes mass production difficult.

Therefore, an object of the present disclosure is to provide a device for improving respiration through the nose which can be easily used.

SUMMARY

This problem is solved by embodiments described herein. A device according to the present disclosure may include at least one nasal insert provided to be inserted into a nostril of a user. The at least one nasal insert comprises a cone-shaped base body and a through-hole extending along the main axis of the base body. Furthermore, the nasal insert comprises a spiral element which is arranged inside the base body and extends from the base of the base body to the tip of the base body. In other words, the spiral element inside the base body runs in the form of a helical line from the base of the base body to its tip. In particular, the outside of the base body may be provided to be in direct contact with the nasal vestibule and/or the nasal cavity when the device is used.

The base body is conical, which herein is understood to be a shape that tapers towards the top in order to adapt to the inside of the nose. In particular, it can be a truncated cone or a truncated pyramid. It can be a straight or an inclined truncated cone or truncated pyramid. The terms "major axis", "base", and "shell" refer in the usual way to the corresponding elements of a cone or pyramid. The "tip" designates the tapered part of the base body.

If the terms "top", "bottom", "vertical" and "horizontal" are used in the following, they also refer to the arrangement of the base body: The base of the base body is at the bottom and the tip is at the top. A vertical direction runs from bottom to top. Accordingly, a horizontal direction runs perpendicular to the vertical.

The base body may comprise an outer wall that corresponds to the shell of the truncated cone or pyramid. The outer wall may be solid. It may also be perforated. In particular, the outer wall may be configured such that it comprises one or more struts that run from the base of the base body to the tip of the base body. The spiral element may be arranged on these struts. In particular, the struts may be connected to each other by means of the spiral element. Such a configuration of the base body is particularly advantageous, since the inner walls of the nose are largely exposed when the device is used, which makes the device comfortable to wear.

The outside of the outer wall may be smooth. The outside may also comprise elevations and/or depressions and/or step-shaped elements.

When using the device, the nasal insert is inserted into a nostril and placed in the nasal vestibule and at least partially in the nasal cavity. When inhaling through the nostril, the respiratory air, which flows through the interior of the base body and over the spiral-shaped element, is put into a rotational movement around the main axis of the base body. The inflowing air column thus begins to rotate around the main axis. This movement results in a suction effect, which increases the amount of respiratory air flowing into the nose.

In other words, one embodiment of a device according to the present disclosure, by its geometrical configuration alone, ensures that the amount of air flowing in during a breath is increased. Thus, for example, an increased recovery effect can be achieved by using the device while sleeping. Furthermore, snoring can also be suppressed. The use of the device can also increase oxygen uptake during sports activities, for example, and thus result in improved performance.

In some embodiments, the through-hole is also conically shaped. The resulting taper of the hole diameter may further enhance the increased-recovery effect described above.

Since a large part of the nasal insert according to embodiments of the present disclosure is located in the nasal vestibule when used, it is easily accessible and can be easily inserted or removed by the user.

Since the above mentioned effect occurs due to the specific geometric configuration of the nasal insert, it is not necessary to adapt the nasal insert individually for each user. The nasal insert can therefore be provided in different standard sizes, for example for children and adults. This allows efficient mass production.

The base body may comprise a thermoplastic material, in particular a natural rubber-based one. In particular, the base body may consist of such a plastic, in particular a thermoplastic elastomer. This has the advantage that the device is well tolerated by the user. Furthermore, such plastics are flexible so that the outer shape of the nasal insert can adapt to the nasal vestibule and/or the nasal cavity. Moreover, the use of such a plastic allows easy cleaning of the device after use.

In particular, the plastic can be free of plasticizers and/or polyphthalamides (PPA). This is advantageous because the nasal insert can be in direct contact with the nasal mucosa. By dispensing with plasticizers, allergic reactions can be prevented. It is also known that plasticizers can be harmful to health, especially for children.

The nasal insert may, for example, be produced by an injection molding process. The nasal insert may be formed of one or more parts.

The base body may have a height of 10 to 50 mm. The diameter or the maximum expansion of the base body at its base in radial direction may be 0.2 to 25 mm. The diameter or the maximum expansion of the base body at its tip in radial direction may be 0.2 to 20 mm. The wall thickness of the base body may be 0.1 to 4 mm. The wall thickness may be constant, but it may also vary along the height of the base body.

The spiral element may have a pitch of 0.1 to 5 mm. Here, the pitch describes the pitch of the above mentioned helical line in the direction of the main axis. The number of turns of the spiral may be between 1 and 20. Such a configuration of the spiral element can be used to generate a vortex-shaped rotary movement of the air in a particularly effective way.

The spiral element may have external dimensions of 0.1 to 5 mm. The cross-sectional shape of the spiral element may be polygonal, circular or elliptical.

The spiral element may also have lamellar structures. Alternatively or additionally lamellar structures may be arranged on the inside of the base body. The lamellar structures may be a bundle of lamellas. Between these lamellas, fine dust, dirt or similar particles contained in the respiratory air can be deposited. This effect is supported by the vortex-shaped rotary movement of the air, due to which the inflowing air is directed towards the inner wall. In other words, the inflowing air can be filtered by the lamellas. The use of one of the above-mentioned plastics can further increase the retention capacity of the lamellas, as very small particles adhere well to these plastics.

The lamellas may extend along a helical line from the base body to its tip. The lamellas may have a height and/or thickness and/or a distance between each other between 0.1 and 4 mm. Such a configuration of the lamellas can achieve a particularly effective filtering of the air.

The lamellas may be arranged vertically or horizontally.

Furthermore, the lamellas may be configured such that they form reservoirs for substances for inhalation. Substances for inhalation may, for example, be substances for the short- and long-term treatment of respiratory diseases, such as bronchitis, flu or flu-like symptoms and/or allergies. Substances for inhalation may also be substances for respiratory relief. It is also possible that the substances are fragrances.

The lamellas may have a triangular cross-sectional profile. In this case, the cross-sectional profile lies in a plane normal to the helical line. The cross-sectional profile of the lamellas may also be rectangular. It is also possible that the lamellas have an undulating or serrated cross-sectional profile.

Furthermore, the height profile of the lamellas may vary in the direction of the helical line. For example, the height profile of the lamellas may be zigzag-shaped or undulated from the base to the tip of the base body along the helical line.

In particular, depressions may be created by an undulating or serrated configuration of the cross-sectional profile and/or the height profile of the lamellas that can serve as reservoirs for the above-mentioned substances for inhalation.

The tip of the base body may be configured to be inserted into a nasal passage. For example, the tip of the base body may be sufficiently flexible due to its material and dimensions to be inserted into a nasal passage like a funnel. The respiratory air can thus flow directly through the nasal insert into the nasal passage. Thereby, a particularly effective conduction of the respiratory air to the nasopharynx can be achieved.

The device may comprise a first nasal insert and a second nasal insert. The first nasal insert may be provided to be inserted into a first nostril of the user. The second nasal insert may be provided to be inserted into the second nostril of the user. This allows the advantageous effect described above to be achieved for both nostrils and thus for both sections of the nasal cavity.

The device may further comprise a connecting element that structurally connects the first nasal insert and the second nasal insert at the base of their respective base bodies. In particular, the connecting element may connect the sides of the nasal inserts facing the nasal septum. The connecting element may, for example, be designed as a bridge or bar. The connecting element may be permanently or detachably connected to the respective nasal inserts.

The connecting element can further improve the handling of the device during use. For example, it can be ensured that the user inserts the nasal inserts correctly into the nostrils, as the connecting element ensures that the nasal inserts have the correct orientation to each other. Furthermore, the connecting element can stabilize the nasal inserts in the nostrils. The connecting element can also facilitate the removal of the device from the nose after use. Furthermore, the connecting element can prevent the loss of one of the two nasal inserts when not in use. It can also facilitate the storage of the device.

In such a device, a first magnet may be arranged on and/or in the outside of the base body at the first nasal insert, wherein the first magnet faces the nasal septum when using the device. Furthermore, a second magnet may be arranged on and/or in the outside of the base body in the second nasal insert, wherein the second magnet faces the nasal septum when the device is used. The poles of the first magnet and the second magnet can be arranged such that there is an attracting force between the first magnet and the second magnet when using the device.

Such a configuration of the device allows the first and second nasal inserts to be "clamped" to the nasal septum to a certain extent due to the force between the magnets. Thus, an easy and safe fixation of the nasal inserts in the user's nose is ensured.

The strength of the magnets may be 50 to 100 mT, for example. Such a strength allows a secure fixation of the nasal inserts without the force having an uncomfortable effect on the user. Such magnets are also easily available in the required size, especially with external dimensions in the range of 0.2 to 10 mm. The magnets can be ferrite magnets, for example. They can also be plastic magnets. In particular, the magnets can be flexible magnets.

The magnets may preferably be embedded in the wall of the base body. For example, the magnets may already be introduced into the wall during the production of the base body. This can be done during injection molding, for example. Embedding the magnets has the advantage that the outside of the wall remains smooth. This makes it comfortable for the user to wear the device.

Alternatively or additionally, it is also possible to fix the magnets on the inside or outside of the wall. In particular, it is possible that a depression or pocket is provided on the outside of the wall, in which a magnet is fixed. This may be done with a suitable adhesive, for example. In particular, this may be a low-solvent adhesive, for example a dispersion adhesive. The adhesive may, for example, be a natural rubber-based adhesive. Such adhesives have the advantage that they are environmentally friendly and harmless to the human organism.

The device comprising the first nasal insert, the second nasal insert and the connecting element may be made in one piece. It can also be made in several parts.

The present disclosure further provides a use of a device for improving respiration, in particular for non-therapeutic performance enhancement by increased oxygen uptake, wherein at least one nasal insert is inserted into the nostril of a human being. The device may have one or more of the features described above.

BRIEF DESCRIPTION OF THE DRAWINGS

Further features and advantages of embodiments of the present disclosure are explained below on the basis of the exemplary Figures. Therein.

DETAILED DESCRIPTION

Figure 1:
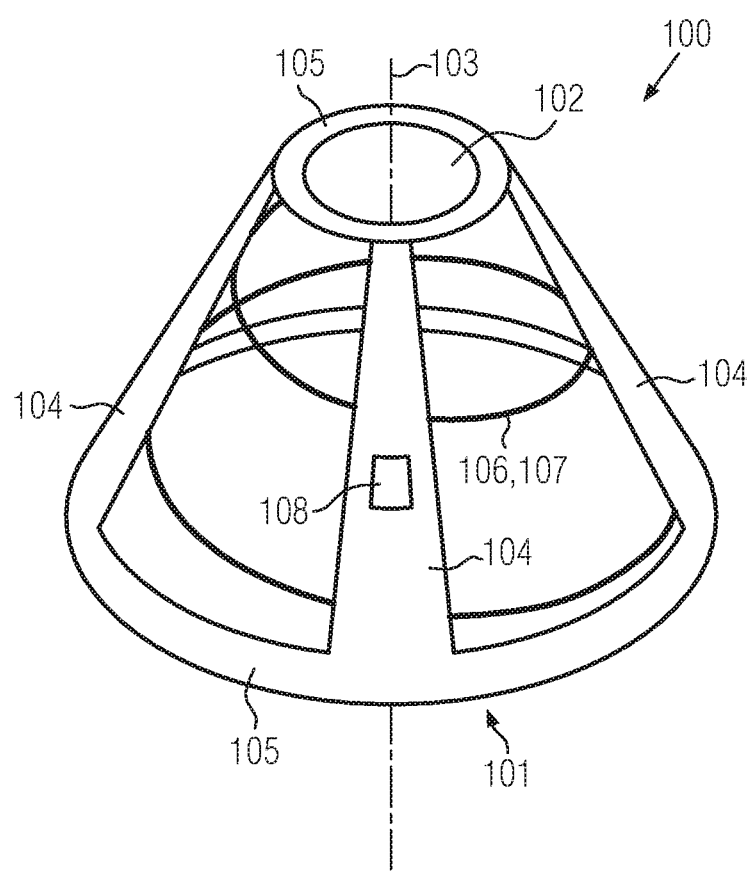
FIG. 1 schematically shows a perspective view of a nasal insert.

FIG. 1 shows an embodiment of a nasal insert 100 for a device 1 to improve the respiration of a user through the nose in perspective view. It can be seen that the nasal insert 100 comprises a conical base body 101. Furthermore, it can be seen that an equally conical through-hole 102 extends through the base body 101 along the main axis 103, which is indicated in FIG. 1 by the dashed line.

In the embodiment shown, the base body 101 includes four struts 104 which run from the base of the base body 101 to its tip. The struts 104 are connected at their base and at their tip by ring-shaped elements 105. These ring-shaped elements 105 can give the base body 101 increased stability, however, they are not necessary for the functioning of the device 1 and can be omitted.

It can further be seen in FIG. 1 that a spiral element 106 is arranged inside the base body. The spiral element 106 runs in a helical line from the base body 101 to its tip. The struts 104 support the spiral element 106. In the embodiment shown, the spiral element 106 includes three turns. It goes without saying, however, that the spiral element 106 can have more or less turns.

The base body 101 and the spiral element 106 of the nasal insert 100 shown in FIG. 1 are made of a plastic material, in particular a natural rubber-based plastic. This makes the nasal insert 100 well tolerated by the user and comfortable to wear. The tip of the base body 101 is flexible enough to be inserted into a user's nasal passage.

In the embodiment shown in FIG. 1, the base body 101 and the spiral element 106 are configured in one piece.

The spiral element 106 also includes lamellas 107 (not shown in FIG. 1) which are described in more detail below with reference to FIGS. 2a to 2c. Lamellas 107 can also be arranged on the inside of the base body 101, in particular on the inside of the struts 104 (not shown in FIG. 1).

FIG. 1 further shows that a magnet 108 is arranged on a strut 104 of the base body 101. The function of the magnet 108 is explained in more detail below with reference to FIG. 4.

Figure 2A:
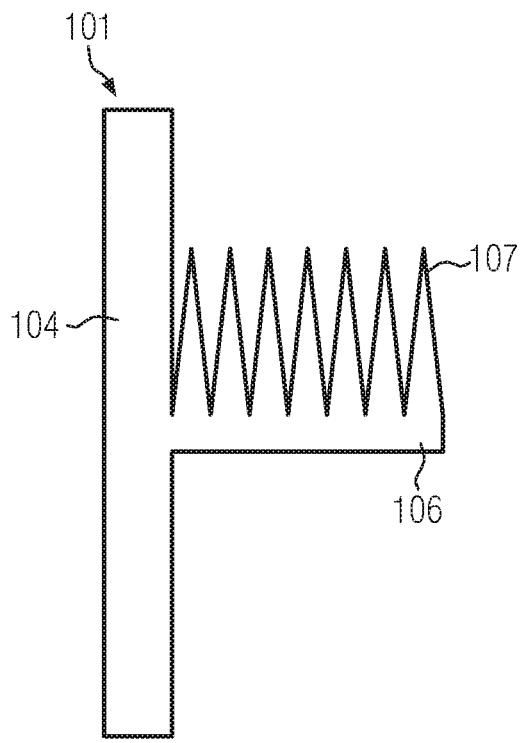
FIGS. 2a to 2e schematically shows a spiral element in sectional view and perspective view.

FIG. 2a schematically shows a sectional view through a spiral element 106. The drawing plane in FIG. 2a is perpendicular to the helical line along which the spiral element 106 runs. FIG. 2a also shows the base body 101 and a strut 104. The spiral element 106 is arranged on the strut 104 inside the base body. FIG. 2a further shows that the spiral element 106 includes lamellas 107. In the embodiment shown, the lamellas 107 are arranged upright on the spiral element 106 and run in the direction of the helical line.

Figure 2B:
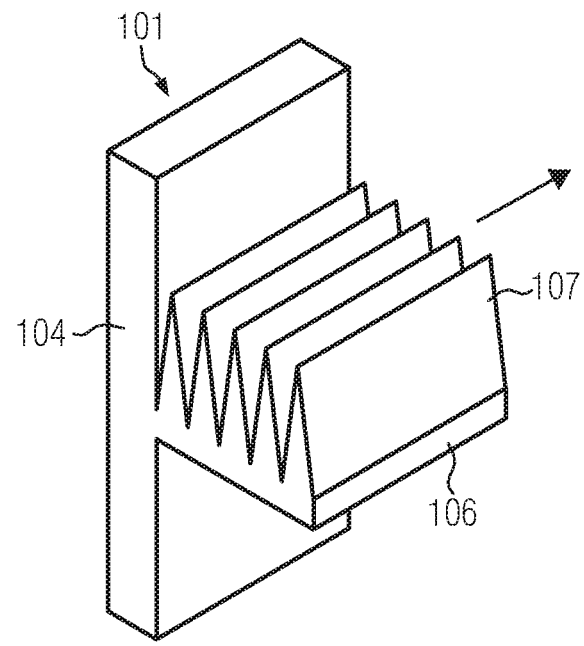

FIG. 2b shows the elements illustrated in FIG. 2a in a perspective view. In FIG. 2b, it can be seen that the lamellas 107 run in the direction of the helical line indicated by the arrow.

In the embodiment shown in FIGS. 2a and 2b, the lamellas 107 are arranged vertically on the spiral element 106. Alternatively or additionally, the lamellas 107 can be arranged vertically below the spiral element 106.

Figure 2C:
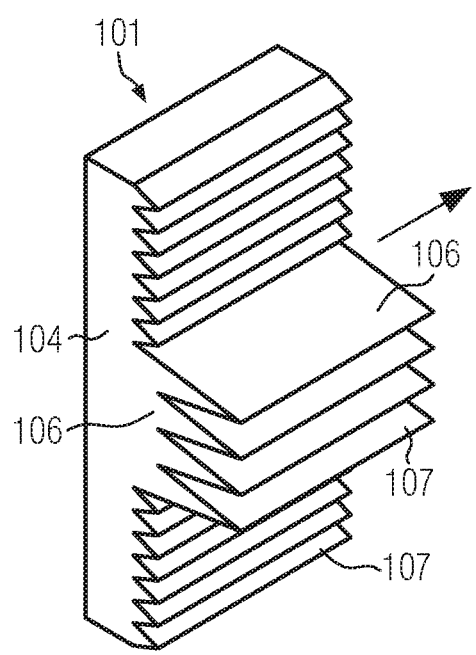

FIG. 2c shows another embodiment of the spiral element in perspective view, with the lamellas 107 arranged horizontally. The drawn arrow again indicates the direction of the helical line. FIG. 2c further shows that lamellas 107 can also be arranged on the inside of the base body 101, in particular on the inside of the struts 104. In the embodiment shown, these run parallel to the lamellas 107 which are arranged on the spiral element 106.

The distance between the lamellas 107 shown in FIGS. 2a to 2c is selected such that particles present in the respiratory air, such as fine dust or pollen, can be retained between the lamellas 107. Thus a filtering of the respiratory air is achieved.

In the lamellas 107 shown in FIGS. 2a to 2c, the thickness of the lamellas 107 decreases from their base to their tip. In other words, the lamellas 107 have a triangular cross-sectional profile. However, other cross-sectional profiles are also possible. It is also possible that the lamellas 107 have a constant thickness, as shown in FIGS. 2d and 2e.

Figure 2D:
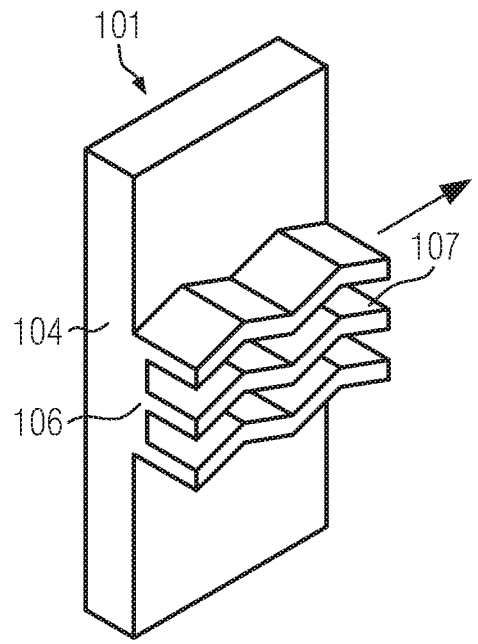

FIG. 2d shows another embodiment of the spiral element in perspective view, with the lamellas 107 arranged horizontally. The drawn arrow again indicates the direction of the helical line. In the embodiment shown in FIG. 2d, the height profile of the lamellas 107 varies in a zigzag fashion in the direction of the helical line. Alternatively, the height profile could also vary in an undulating manner.

Figure 2E:
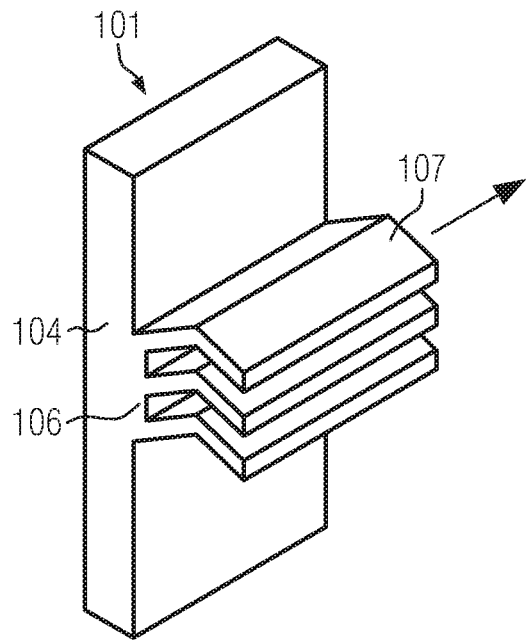

FIG. 2e shows another embodiment of the spiral element in perspective view, with the lamellas 107 arranged horizontally. The drawn arrow again indicates the direction of the helical line. In this embodiment, the cross-sectional profile of the lamellas 107 is roof-shaped.

In the embodiments shown in FIGS. 2d and 2e, additional lamellas may also be arranged on the inside of the base body 101, in particular on the inside of the struts 104 (not shown).

Furthermore, between the lamellas 107 substances for inhalation may be stored (not shown). In other words, the lamellas 107 may serve as a reservoir for the substances for inhalation. In the embodiment shown in FIGS. 2a and 2b, substances may be stored between the vertically arranged lamellas 107. In the embodiments shown in FIGS. 2d and 2e, the substances may be stored in the depressions formed by variation of the height profile or cross-section.

Figure 3:
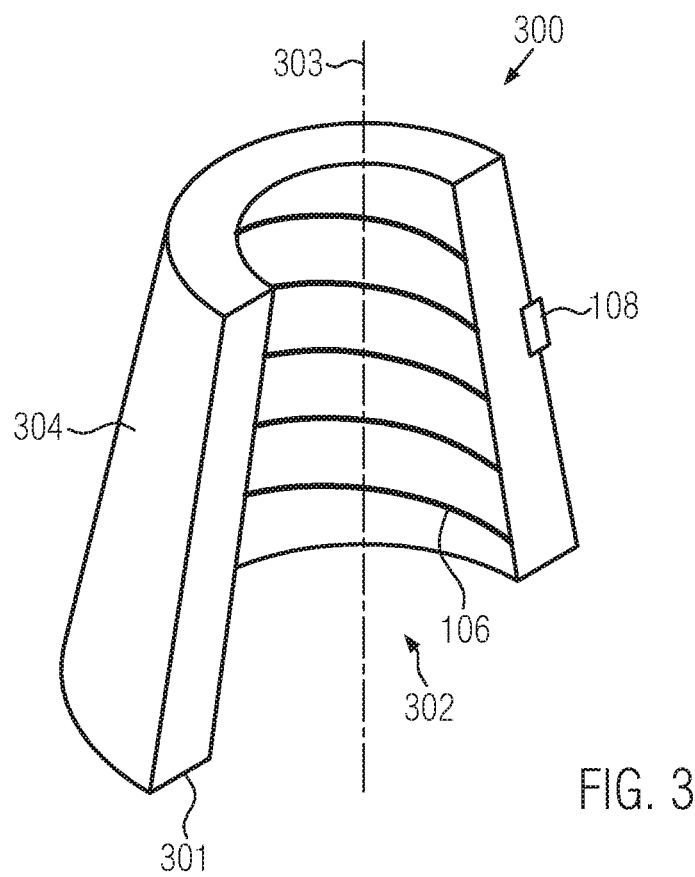
FIG. 3 schematically shows a sectional view through an embodiment of a nasal insert.

FIG. 3 shows an alternative embodiment of a nasal insert 300 for a device 1 to improve the respiration of a user through the nose in sectional view. It can be seen that the nasal insert 300 includes a conical base body 301. Furthermore, it can be seen that an equally conical through-hole 302 extends through the base body 301 along the main axis 303, which is indicated by the dashed line in FIG. 3.

The nasal insert 300 shown in FIG. 3 is made of a plastic material, in particular a natural rubber-based plastic. This makes the nasal insert 300 well tolerated by the user and comfortable to wear. The tip of the base body 301 has sufficient flexibility to be inserted into a user's nasal passage.

The base body 301 and the through-hole 302 form the wall 304 of the base body 301. Inside the base body there is arranged a spiral element 106 which runs along a helical line from the base of the base body 301 to the tip of the base body 301. In the embodiment shown, the spiral element 106 has five turns. However, it goes without saying that the spiral element 106 can have more or less turns.

FIG. 3 further shows that a magnet 108 is arranged on an outer side of the base body 301. The function of the magnet 108 is explained in more detail below with reference to FIG. 4.

The cone-shaped base body 301 shown in FIG. 3 has the shape of a straight truncated cone. However, it is also possible that the base body 301 has the shape of an inclined truncated cone. For example, the truncated cone may be inclined to the side that is inclined towards the nasal septum when using the nasal insert 300. In this case it is advantageous if the magnet 108 is arranged on this side. Other geometric forms that have an upwardly tapering structure are also possible forms for the base body 301.

The spiral element 106 shown in FIG. 3 can be configured like the spiral element described above. In particular, it may include lamellas 107 as shown in FIGS. 2a to 2e.

In the embodiment shown in FIG. 3, too, lamellas can be arranged on the inside of the wall 304. Here, the lamellas can also be arranged along a helical line from the base body 301 to its tip, according to the embodiment shown in FIG. 2c.

Figure 4:
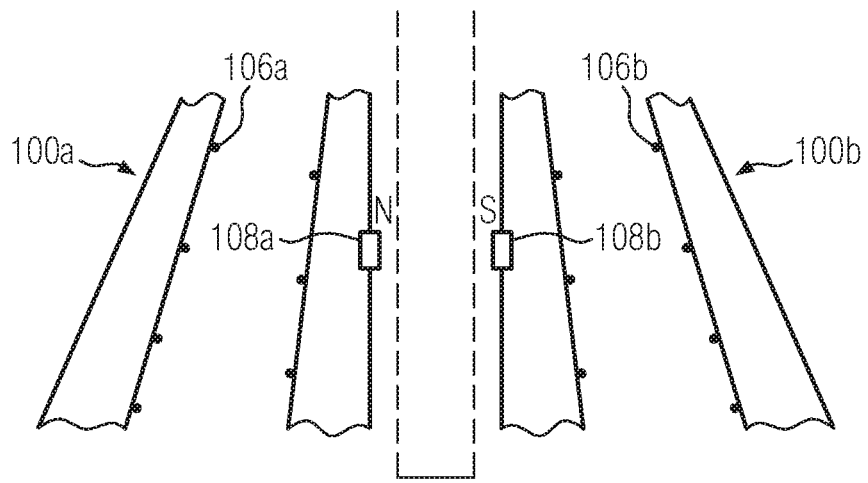
FIG. 4 schematically shows a sectional view of an embodiment of the device that includes two nasal inserts in side view.

FIG. 4 schematically shows a section of an embodiment of a device 1 for improving respiration in lateral sectional view. FIG. 4 illustrates a situation in which the nasal inserts 100a and 100b have been inserted into the nostrils of a user.

The device 1 shown includes two nasal inserts 100a and 100b which are configured to be inserted into the two nostrils of a user. Here, in principle, the nasal inserts 100a and 100b can correspond to the nasal insert 100 shown in FIG. 1 or the nasal insert 300 shown in FIG. 3. The respective spiral elements 106a and 106b and the magnets 108a and 108b can be seen. The nasal inserts 100a and 100b differ in the embodiment shown in the arrangement of magnets 108a and 108b. For example, the north pole of the magnet 108a is facing outwards, while the magnet 108b is arranged with its south pole facing outwards.

The section of the nasal inserts 100a and 100b shown in FIG. 4 shows the surroundings of the magnets 108a and 108b. Furthermore, the user's nasal septum is indicated by the dashed lines. It can be seen that the outer walls of the nasal inserts 100a and 100b are pressed against the nasal septum due to the magnetic attraction between the north pole of the magnet 108a and the south pole of the magnet 108b. Thus a secure hold of the nasal inserts 100a and 100b in the nose is achieved.

In alternative embodiments, several magnets 108 may also be arranged in the wall of a nasal insert. For example, it is possible that a row of magnets 108 extends from the base body to the tip of the base body.

Figure 5:
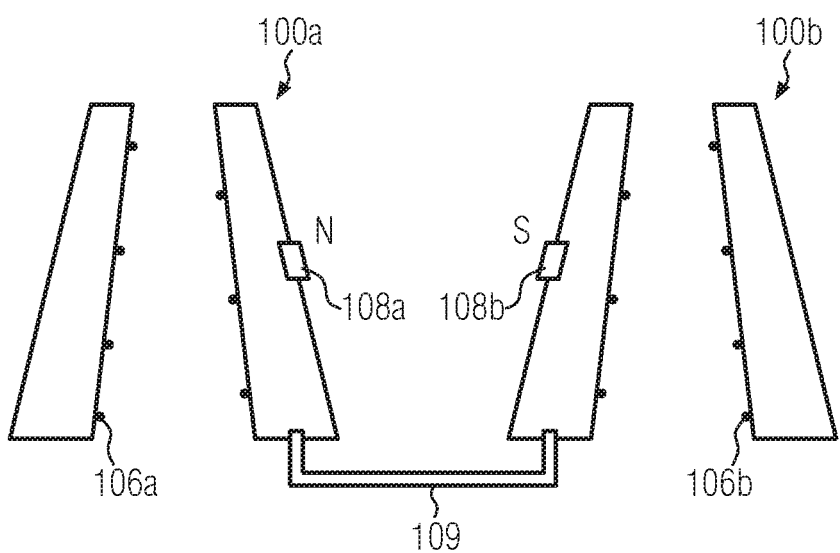
FIG. 5 schematically shows an embodiment of a device where two nasal inserts are connected to each other in side view.

FIG. 5 shows another embodiment of a device 1 for improving respiration in a side view. This embodiment includes the same elements as the embodiments shown in FIGS. 1 to 4, which are not described again in detail here. Here, in principle, the nasal inserts 100a and 100b may each correspond to the nasal insert 100 shown in FIG. 1 or to the nasal insert 300 shown in FIG. 3. In the device illustrated in FIG. 5, further a connecting element 109 is provided, which connects the nasal inserts 100a and 100b at their respective bases. It can be seen that the connecting element 109 connects those sides of the nasal inserts 100a and 100b with each other on which the magnets 108a and 108b are arranged.

The connecting element 109 on the one hand ensures that the user inserts the nasal inserts 100a and 100b into the nostrils in the correct orientation. In particular, the magnets 108a and 108b are automatically facing each other due to the connection by the connecting element 109. Furthermore, the connecting element 109 can stabilize the nasal inserts 100a and 100b inserted into the nostrils when using the device 1. The connecting element 109 can also help to remove the device 1 from the nose after use. For example, the user can use the connecting element 109 to pull the nasal inserts 100a and 100b out of the respective nostrils. Furthermore, the connecting element 109 can prevent that one of the nasal inserts 100a and 100b is lost in the situation where the device 1 is not in the user's nose. This also facilitates the storage of the device 1.

In the embodiment shown in FIG. 5, the connecting element 109 is permanently connected to the nasal inserts 100a and 100b. However, it is also possible that the connecting element 109 is an independent element which is detachably connected to the nasal inserts 100a and 100b. This can be achieved, for example, by means of a suitable plug-in connection which connects the connecting element 109 with the nasal inserts in a positive and/or non-positive manner. For example, the ends of the connecting element 109 may be configured pin-shaped and provided to be inserted into a corresponding opening or eyelet in the nasal inserts 100a and 100b. Such connection possibilities are known, for example, from security threads used to attach labels.

When using the device 1, the user first inserts the nasal insert 100a into one of his nostrils and the nasal insert 100b into the other nostril. The user can insert the nasal inserts in such a way that the tip of the nasal insert 100a and/or the tip of the nasal insert 100b is inserted into a respective nasal passage.

Due to the force of attraction between the magnets 108a and 108b, the device is clamped to the user's nasal septum. The user can then inhale through his nostrils, whereby the respiratory air is put into a rotary movement due to the spiral elements 106a and 106b, thus achieving a suction effect and increased air supply through the nose in the manner described above.

The device 1 can remain in the nose at the user's discretion. For example, it is possible to wear the device 1 during sleep.

To remove the device 1, the user grasps the nasal inserts 100a and 100b and pulls them out of their respective nostrils. This can also be done by using the connecting element 109.

After use, the device 1 can be easily cleaned with water and/or detergent and/or ultrasonic cleaning.

It goes without saying that features mentioned in the embodiments described above are not limited to these special combinations and are also possible in any other combinations. Furthermore, it goes without saying that geometries shown in the Figures are only exemplary and are also possible in any other configurations.

The invention claimed is:

1. A device for improving respiration, comprising:
    at least one nasal insert configured to be inserted into a nostril of a user,
    wherein the at least one nasal insert comprises:
        a conical base body;
        a through-hole extending along a main axis of the base body; and
        a spiral element arranged inside the base body and extending from a base of the base body to a tip of the base body;
        wherein the spiral element comprises lamellar structures arranged on the spiral element and configured so as to form reservoirs for substances for inhalation.

2. The device of claim 1, wherein the spiral element has a pitch of 0.1 to 5 mm and/or wherein the spiral element has a number of turns of 1 to 20.

3. The device of claim 1, wherein the base body comprises one or more struts on which the spiral element is arranged.

4. The device of claim 1, wherein the lamellar structures extend along a helical line from the base to the tip of the base body.

5. The device of claim 1, wherein the lamellar structures have a height and/or thickness and/or a distance between each other of between 0.1 and 4 mm.

6. The device of claim 1, wherein the at least one nasal insert comprises a first nasal insert and a second nasal insert.

7. The device of claim 6,
    wherein a first magnet is arranged on and/or in an outer side of the base body in the first nasal insert, wherein the first magnet is configured to face the nasal septum when the device is used,
    wherein a second magnet is arranged on and/or in an outer side of the base body in the second nasal insert, wherein the second magnet is configured to face the nasal septum when the device is used, and
    wherein poles of the first magnet and the second magnet are arranged such that an attracting force exists between the first magnet and the second magnet when the device is used.

8. The device of claim 6, further comprising a connecting element which connects the first nasal insert and the second nasal insert to each other at the base of their respective base bodies.

9. The device of claim 1, wherein the base body of the at least one nasal insert has a height of 10 to 50 mm and/or wherein a wall of the at least one nasal insert has a thickness of 0.1 to 4 mm.

10. The device of claim 1, wherein a diameter of the base body of the at least one nasal insert at its base is 0.2 to 25 mm and/or the diameter of the base body of the at least one nasal insert at its tip is 0.2 to 20 mm.

11. The device of claim 1, wherein the base body includes a thermoplastic material, in particular a natural rubber-based one.

12. A method for improving respiration, the method comprising inserting the nasal insert of the device of claim 1 into the nostril of a user.

* * * * *